United States Patent [19]

Tomisawa et al.

[11] Patent Number: 4,541,959
[45] Date of Patent: Sep. 17, 1985

[54] DIPHENYLSULFIDE DERIVATIVES

[75] Inventors: Kazuyuki Tomisawa, Saitama; Kazuya Kameo; Toru Matsunaga, both of Ageo; Shiuji Saito, Niiza; Yoshimoto Nakashima, Ageo; Kaoru Sata, Tokorozawa, all of Japan

[73] Assignee: Taisho Pharmaceutical Co., Ltd., Tokyo, Japan

[21] Appl. No.: 645,356

[22] Filed: Aug. 29, 1984

[30] Foreign Application Priority Data

Aug. 31, 1983 [JP] Japan ................... 58-159955

[51] Int. Cl.$^4$ ........................... C07C 153/023
[52] U.S. Cl. ................................. 260/455 R
[58] Field of Search ............. 260/455 R; 560/15; 562/426

[56] References Cited

U.S. PATENT DOCUMENTS 4,435,588  3/1984  Liu ........................ 260/455 R

Primary Examiner—Henry R. Jiles
Assistant Examiner—Robert C. Whittenbaugh
Attorney, Agent, or Firm—Cushman, Darby & Cushman

[57] ABSTRACT

Diphenylsulfide derivatives represented by the general formula

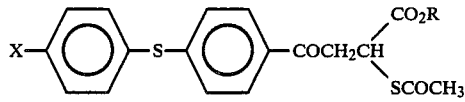

wherein, X represents a hydrogen atom, a chlorine atom or a methyl group, and R represents a hydrogen atom or a lower alkyl group. These diphenyl sulfides reduce lipids such as cholesterols and triglycerides in the blood of mammals.

7 Claims, No Drawings

DIPHENYLSULFIDE DERIVATIVES

BACKGROUND OF THE INVENTION

This invention relates to novel diphenylsulfide derivatives, and more particularly, it relates to diphenylsulfide derivatives having an effect to reduce the amount of lipid such as total cholesterols and triglycerides in blood of mammals.

Generally, the sedimentation of excess amounts of lipids in blood is considered to be a cause of arteriosclerosis such as atherosclerosis. Accordingly, the reduction of the lipid concentration in blood is considered to be a desirable means for the therapy of arteriosclerosis and the diseases related thereto.

As a result of earnest studies, the present inventors have found that certain diphenylsulfide derivatives extremely reduce lipids such as total choresterols and triglycerides in blood of mammals and exhibit weak side effect, and thus the present invention has been completed.

SUMMARY OF THE INVENTION

An object of the present invention is to provide novel diphenylsulfide derivatives having an effect to reduce the amount of lipid such as total cholesterols and triglycerides in blood of mammals.

Other objects and advantages of the present invention will be apparent from the following descriptions.

DETAILED DESCRIPTIONS OF THE INVENTION

The present invention is illustrated in detail hereunder.

The objective compounds of the present invention are diphenylsulfide derivatives (hereinafter referred to as Compound I) represented by the general formula

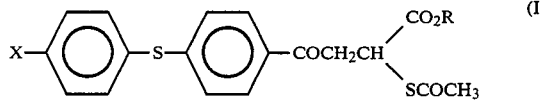

wherein, X represents a hydrogen atom, a chlorine atom or a methyl group, and R represents a hydrogen atom or a lower alkyl group.

The lower alkyl group for R are a methyl group, an ethyl group and the like.

The compound I can be prepared, for example, by the following method.

(1) A compound represented by the general formula

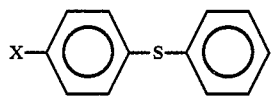

(wherein, X is as defined above) is reacted with maleic anhydride according to Friedel-Crafts reaction to give a carboxylic acid (hereinafter referred to as Compound II) represented by the general formula

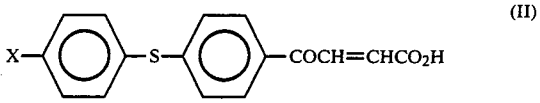

(wherein, X is as defined above).

(2) The compound II is reacted with a conventional alkylating agent having the lower alkyl group as defined for the above R (e.g., alkyl halides, dialkyl sulfates and the like) in an organic solvent (e.g., acetone, dimethylformamide, hexamethylphosphoric triamide, dimethylsulfoxide and the like) in the presence of a base (e.g., sodium carbonate, potassium carbonate, lithium carbonate, sodium hydrogen-carbonate, potassium hydrogen carbonate, sodium hydroxide, potassium hydroxide, sodium alkoxide, sodium hydride and the like) to give an ester compound (hereinafter referred to as Compound III) represented by the general formula

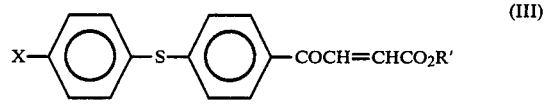

(wherein, X is as defined above, and R' represents the lower alkyl group as defined for the above R).

(3) The compound II or III is dissolved in an organic solvent (e.g., methanol, ethanol, tert-butanol, hexane, benzene, toluene, diethyl ether, dimethoxyethane, dioxane, methylene chloride, chloroform, carbon tetrachloride, carbon disulfide, acetone, ethyl acetate, dimethylformamide, hexamethylphosphoric triamide, dimethylsulfoxide and the like) and thioacetic acid is added in an amount of equimolar to two times the compound II or III. The mixture is reacted at $-20°$ to $50°$ C. for 0.5 to 24 hours to give the compound I.

The compound I exhibits a good hypolipidemic effect in blood of mammals such as rats, rabits and human, and possesses low toxicity, and therefore they are useful as medicine. For the purposes, the compound of the present invention may be administered orally or parenterally in a conventional dosage form such as tablets, capsules, powders, granules, syrups, and injectional forms prepared according to conventional pharmaceutical practices.

The effective dosage of the compound of the present invention depends on the age, weight or response of the patient. Generally, however, the daily dosage in adults may range from 0.1 to 3 g, preferably 0.3 to 1.5 g in single or divided doses.

The preferred compounds of the present invention are the compounds of formula I wherein X is a hydrogen atom or a chlorine atom, and R is a hydrogen atom or an ethyl group.

The present invention is hereinafter concretely illustrated below by Experiments and Examples, but the invention is not limited thereto.

EXPERIMENT 1

5 weeks old male Wister rats (body weight: $120\pm6$ g) were bred for a week at constant temperature and constant humidity, and five rats were used per each group. As a comparative drug, was used clofibrate [chemical name: ethyl 2-(4-chlorophenoxy)-2-methylpropionate]. Suspensions of the compounds I and the comparative drug in a 5% gum arabic solution were used as test compounds, respectively. Each of these test compounds was administered orally to rat of each group in a daily dose of 100 mg/kg as the active component for the continual 3 days. Similarly, a 5% gum arabic solution only was administered orally to rat as control. After administration of the test compound, rats were fasted for 18 hours and anesthetized with diethyl ether. Blood was collected through groin artery and groin vein, and lipid volume in serum was determined using autoanalizer.

Liver was removed at the same time, and its relative weight (ratio to body weight) was determined.

In the following table are shown the blood lipid decreasing rates (percent of the difference of the lipid concentration between the dosed group and the control group) and the liver weight increasing rates (similar percent of the difference of the relative liver weight) by administration of the compound I and the comparative drug.

| Compound number | Blood lipid decreasing rate (%) | | Liver weight increasing rate (%) |
|---|---|---|---|
| | Cholesterol | Triglyceride | |
| 1 | 38.0*** | 13.6 | 5.5 |
| 3 | 38.8*** | 32.9** | 4.5 |
| 5 | 42.1*** | 8.2 | 1.5 |
| Comparative drug | 52.6*** | 8.6 | 25.7*** |

Note
(1) Compound number means a compound which is prepared in the following Example attached the same number of Example as that of the compound in Table.
(2) **significant at 1% of levels of significance.
***significant at 0.1% of levels of significance.

EXPERIMENT 2

Acute Toxicity Text

Male, 8 weeks old ICR mice (body weight of 28–32 g, 8 mice per each group) were administered orally with a suspension of the compound of Example 1 in 5% gum arabic solution, and observed for 7 days, and the $LD_{50}$ value was calculated.

The $LD_{50}$ value of the compound of Example 1 was excess of 1000 mg/kg.

EXAMPLE 1

In 100 ml of dichloromethane were dissolved 5.58 g of diphenylsulfide and 2.99 g of maleic anhydride. To the resulting solution was added gradually 5.97 g of anhydrous aluminum chloride, thereafter the stirring was carried out at room temperature for 5 hours. The reaction solution was concentrated under reduced pressure and poured into a mixture of 5 ml of conc. hydrochloric acid and 100 g of ice, and the mixture was extracted with ethyl acetate. The organic layer was washed with water and dried over magnesium sulfate, and the ethyl acetate was removed by evaporation under reduced pressure. The residue was recrystallized from a mixture of hexane and ethyl acetate to give 6.56 g of 3-(4-phenylthiobenzoyl)acrylic acid.

m.p. 157°–159° C.

(2) To a solution of 2.84 g of 3-(4-phenylthiobenzoyl)acrylic acid in 30 ml of chloroform was added 0.8 ml of thioacetic acid, and the resulting mixture was stirred for 5 hours at room temperature. The chloroform was removed from the mixture by evaporation under reduced pressure, and the residue was purified by silica gel column chromatography (eluent: hexane-ethyl acetate) and then recrystallized from a mixture of hexane and ethyl acetate to give 3.24 g of 2-acetylthio-3-(4-phenylthiobenzoyl)propionic acid.

m.p. 116.5°–118.5° C.

Elementary Anal. for $C_{18}H_{16}O_4S_2$. Calcd. (%): C 59.98, H 4.47. Found (%): C 59.76, H 4.54.

EXAMPLE 2

(1) To a solution of 8.53 g of 3-(4-phenylthiobenzoyl)acrylic acid in 50 ml of dimethylformamide were added 4.54 g of dimethyl sulfate and 2.50 g of potassium carbonate, and the resulting mixture was stirred at room temperature for 3 hours. To the reaction solution was added water, and the mixture was extracted from diethyl ether. The organic layer was washed, in turn, with water, a saturated aqueous solution of sodium hydrogen-carbonate and water, and dried over magnesim sulfate. The diethyl ether was removed from the solution by evaporation, and the residue was recrystallized from a mixture of hexane and dichloromethane to give 6.80 g of methyl 3-(4-phenylthiobenzoyl)acrylate.

m.p. 85°–86.5° C.

(2) To a solution of 2.98 g of methyl 3-(4-phenylthiobenzoyl)acrylate in 30 ml of diethyl ether was added 0.8 ml of thioacetic acid, and the resulting mixture was stirred at room temperature for 5 hours. The reaction solution was washed, in turn, with water, a saturated aqueous solution of sodium hydrogencarbonate and water, and dried over magnesium sulfate. The diethyl ether was removed from the solution by evaporation, and the residue was purified by silica gel column chromatography (eluent: hexane-diethyl ether) to give 3.73 g of methyl 2-acetylthio-3-(4-phenylthiobenzoyl)propionate as an oil.

$IR\nu_{max}^{CHCl_3}$ cm$^{-1}$: 1735 (ester, thioester) 1680 (ketone).

NMR (CDCl$_3$), ppm: 2.36 (3H, s), 3.49 (1H, dd, J=18 Hz, 6 Hz), 3.65 (1H, dd, J=18 Hz, 8 Hz), 3.74 (3H, s), 4.72 (1H, dd, J=8 Hz, 6 Hz), 7.21 (2H, d, J=9 Hz), 7.40–7.52 (5H, m), 7.79 (2H, d, J=9 Hz)

EXAMPLE 3

(1) Following the procedure of Example 2(1) using 5.55 g of diethyl sulfate in place of dimethyl sulfate, there was obtained 7.77 g of ethyl 3-(4-phenylthiobenzoyl)acrylate.

m.p. 74°–75° C.

(2) Following the procedure of Example 2(2) using 3.12 g of ethyl 3-(4-phenylthiobenzoyl)acrylate in place of methyl 3-(4-phenylthiobenzoyl)acrylate, there was obtained 3.46 g of ethyl 2-acetylthio-3-(4-phenylthiobenzoyl)propionate.

m.p. 71.5°–72.5° C.

Elementary Anal. for $C_{20}H_{20}O_4S_2$. Calcd. (%); C 61.82, H 5.19. Found (%): C 61.81, H 5.25.

EXAMPLE 4

Following the procedure of Example 1(1) using 6.00 g of p-methyldiphenylsulfide in place of diphenylsulfide, there was obtained 3.30 g of 3-[4-(4-methylphenylthio)benzoyl]acrylic acid as an amorphous solid.

$IR\nu_{max}^{KBr}$ cm$^{-1}$:1700 (carboxylic acid), 1665 (ketone).

NMR (CDCl$_3$), ppm: 2.41 (3H, s), 6.86 (1H, d, J=16 Hz), 7.18 (2H, d, J=9 Hz), 7.26 (2H, d, J=9 Hz), 7.45 (2H, d, J=9 Hz), 7.86 (2H, d, J=9 Hz), 7.93 (1H, d, J=16 Hz).

(2) Following the procedure of Example 1(2) using 2.98 g of 3-[4-(4-methylphenylthio)benzoyl]acrylic acid in place of 3-(4-phenylthiobenzoyl)acrylic acid, there was obtained 1.93 g of 2-acetylthio-3-[4-(4-methylphenylthio)benzoyl]propionic acid.

m.p. 127°–129° C.

Elementary Anal. for $C_{19}H_{18}O_4S_2$. Calcd. (%): C 60.94, H 4.84. Found (%): C 60.67, H 5.04.

EXAMPLE 5

Following the procedure of Example 1(1) using 6.62 g of p-chlorodiphenylsulfide in place of diphenylsulfide, there was obtained 6.97 g of 3-[4-(4-chlorophenylthio)benzoyl]acrylic acid.

m.p. 164°–165° C.

(2) Following the procedure of Example 1(2) using 3.19 g of 3-[4-(4-chlorophenylthio)benzoyl]acrylic acid in place of 3-(4-phenylthiobenzoyl)acrylic acid, there was obtained 3.67 g of 2-acetylthio-3-[4-(4-chlorophenylthio)benzoyl]propionic acid.

m.p. 111°–114° C.

Elementary Anal. for $C_{18}H_{15}ClO_4S$. Calcd.(%): C 54.75, H 3.83. Found (%): C 54.95, H 4.01.

What is claimed is:

1. Diphenylsulfide derivatives represented by the general formula

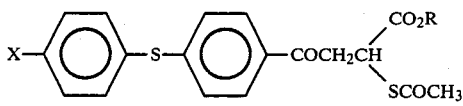

wherein, X represents a hydrogen atom, a chlorine atom or a methyl group, and R represents a hydrogen atom or a lower alkyl group.

2. The diphenylsulfide derivatives as claimed in claim 1, wherein the lower alkyl group is a methyl group or an ethyl group.

3. 2-Acetylthio-3-(4-phenylthiobenzoyl)propionic acid.

4. Methyl 2-acetylthio-3-(4-phenylthiobenzoyl)propionate.

5. Ethyl 2-acetylthio-3-(4-phenylthiobenzoyl)propionate.

6. 2-Acetylthio-3-[4-(4-methylphenylthio)benzoyl]propionic acid.

7. 2-Acetylthio-3-[4-(4-chlorophenylthio)benzoyl]propionic acid.

* * * * *